United States Patent

Watling et al.

[11] Patent Number: 5,206,009
[45] Date of Patent: Apr. 27, 1993

[54] NON-AEROSOL, LOW VOC, PUMP HAIR SPRAY COMPOSITION

[75] Inventors: Ian A. Watling, Surrey; Daksha Patel, Middlesex; Peter J. Petter, Berkshire, all of England

[73] Assignee: ISP Investments Inc., Wilmington, Del.

[21] Appl. No.: 899,835

[22] Filed: Jun. 17, 1992

[51] Int. Cl.⁵ ............................................. A61K 7/11
[52] U.S. Cl. ........................................ 424/45; 424/47; 424/70; 424/71; 424/DIG. 1; 424/DIG. 2; 424/78.02; 424/78.33; 424/78.36
[58] Field of Search ............................. 424/45, 70–71, 424/DIG. 1, DIG. 2; 252/372

[56] References Cited

U.S. PATENT DOCUMENTS 3,694,546  9/1972  Roth et al. .............................. 424/45
3,928,558  12/1975  Cheeseman et al. ................... 424/71
4,134,968  1/1979  Stebles .................................... 424/45

OTHER PUBLICATIONS

Merck Index, 11th ed, Budavari et al. Eds, Merch & Co. Rayway, N.J. 1989 p. 449.

Primary Examiner—Thurman K. Page
Assistant Examiner—Edward J. Webman
Attorney, Agent, or Firm—Walter Katz; Marilyn J. Maue; Joshua J. Ward

[57] ABSTRACT

A non-aerosol, low VOC, pump hair spray composition containing dimethoxymethane as cosolvent is described herein. The composition is applied by the user as a fine spray mist which dries rapidly on the hair, and provides a low curl droop and effective curl retention properties thereon. The composition consists essentially of a hair fixative polymer and a solvent mixture of alcohol, water and dimethoxymethane.

4 Claims, No Drawings

NON-AEROSOL, LOW VOC, PUMP HAIR SPRAY COMPOSITION

BACKGROUND OF THE INVENTION

Non-aerosol and aerosol hair spray compositions contain volatile hydrocarbons and/or dimethylether as propellants for the hair fixative polymers therein. These organic compounds also act as cosolvents with ethanol therein for the hair fixative polymers in the composition. However, due to the problem of flammability, and also the growing concern that emission of such organic compounds into the atmosphere can harm the environment, low volatile organic compound (VOC)-containing hair spray systems now are or will be required in many states in the U.S. However, addition of water in such hair sprays to lower the percentage of VOC compounds usually results in longer drying times and poorer overall performance. Furthermore, the hair style may "droop" due to relaxation of the curls by the water present during the required extended drying period.

Accordingly, it is an object of this invention to provide low VOC hair spray compositions having advantageous drying times and curl droop properties.

SUMMARY OF THE INVENTION

A non-aerosol, low VOC, pump hair spray composition is provided herein which is capable of being applied by the user as a fine spray mist, which dries rapidly on the hair, and which provides low curl droop and effective curl retention properties thereon. The composition consists essentially of a hair fixative polymer, and a mixture of alcohol, water and dimethoxymethane (DMM) as cosolvents therefor.

Preferably, the hair fixative polymer is present at a solids level of about 1–15%, the alcohol in an amount of about 50–70%, water at 10–30%, and DMM at 10–30%, by weight of the composition.

DETAILED DESCRIPTION OF THE INVENTION

The hair fixative polymers used in the compositions of the invention were formulated at 4 to 10% solids into defined base systems. The compositions then were tested in packs fitted with a Calmar Mistette Mark II pump, with yellow (high viscosity) orifice. The test sprays were evaluated for the following characteristics.

1—Spray patterns
2—Drying time
3—Curl droop
4—Curl retention
5—Hair characteristics on tresses
6—Film clarity on glass These properties were tested by standard procedures, except for curl droop, which was measured in the manner described hereinafter.

The following base systems were used for the hair spray formulations of the invention:
(a) 60:20:20 ethanol:water:DMM (dimethoxymethane) - Lambiotte (Belgium)
(b) 80:20 ethanol:water
(c) 100% ethanol.

The following hair fixative polymers were formulated into the above base systems to a 10% solids level.
A. PVP/VA E-335 (polyvinylpyrrolidone-vinyl acetate) - International Specialty Products
B. PVP/VA E-735 (polyvinylpyrrolidone-vinyl acetate) - ISP
C. Gantrez ES-225 - (neutralized 10% with AMP aminomethylpropanol) - ISP
D. Gantrez ES-425 - (neutralized 10% with AMP) - ISP
E. Gantrez SP-215 - (neutralized 10% with AMP) - ISP
F. Advantage CP - (neutralized 10% with AMP) - ISP
G. Copolymer VC-713 (vinylpyrrolidone/vinyl caprolactam/dimethylamino ethyl methacrylate) - ISP The results are shown below.

1. Spray Patterns

A fine spray was obtained for all compositions A through G.

2. Drying Times

Drying time was measured by spraying the test composition from a distance of 25 cm onto an alcohol-sensitive paper during a single pump stroke. The time taken for the spray pattern to dry gave a relative drying time for the composition.

The results are summarized in Table I below.

Faster drying times were obtained when dimethoxymethane (DMM) was present in the formulation. The reduction in drying times for DMM-containing formulation over other solvents was about 50%.

These laboratory tests were followed up by observations of the drying times on actual hair tresses which indicated that the presence of DMM in the composition produced a substantial reduction in drying times when such compositions were applied onto hair.

TABLE I

| Resin System | | Solvent System Drying times (seconds) | | Results % Reduction in Drying Times |
|---|---|---|---|---|
| Hair Fixative Polymer | % Solids | In 80:20 (% by wt) Ethanol:Water | In 60:20:20% (% by wt) Ethanol:Water:DMM | with DMM-containing Solvent System |
| PVP/VA E-335 | 5 | 91 | 72 | −20 |
| | 10 | 518 | 329 | −36 |
| PVP/VA E-735 | 5 | 141 | 90 | −36 |
| | 10 | 376 | 365 | −3 |
| Gantrez ES-225 | 3 | 210 | 103 | −51 |
| | 4 | 275 | 196 | −29 |
| Gantrez ES-425 | 5 | 309 | 128 | −59 |
| | 10 | 262 | 210 | −20 |
| Gantrez SP-215 | 3 | 48 | 46 | −4 |
| | 4 | 100 | 46 | −54 |
| Advantage CP | 5 | 66 | 46 | −30 |
| | 10 | 320 | 93 | −70 |
| Copolymer VC-713 | 5 | 257 | 132 | −49 |
| | 10 | 572 | 308 | −46 |

3. Curl Droop

A minimum of 8 hair tresses per formulation was used. Each tress was thoroughly wetted with lukewarm tap water. The curl was prepared by flattening the tress and rolling along a mandrel, clipping a bobby pin to the tight curl, and drying the curls completely under a dryer for 0.5-1 hr. The treated tresses were hung on a calibrated plexiglass rack and the top of the tress was adjusted to the zero line. The length of the curl was recorded as the lowest graduation reached by the curl (Lo). The curls were removed from the rack and each side sprayed with a test formulation from a distance of 8 inches for 2 seconds. The curl was returned to its original position on the rack and air dried for 10 minutes under ambient conditions. A second reading (L) gave the amount of curl droop (% increase in curl length) caused by the application of the test product, by the formula below:

$$\% \text{ Curl Droop} = \frac{(L - Lo)}{L} \times 100\%$$

The results, shown in Table II below, established that curl droop increased when water was added to ethanol, but decreased when DMM was present as a cosolvent.

TABLE II

| | Curl Droop | | |
|---|---|---|---|
| | Base Solvent System | | |
| Hair Fixative Polymer | 100% Ethanol | 80:20 Ethanol:water | 60:20:20 Ethanol:water:DMM |
| PVP/VA E-335 | 14 | 60 | 48 |
| Gantrez SP-215 | 17 | 44 | 42 |
| Advantage CP | 24 | 70 | 48 |
| Copolymer VC-713 | 28 | 60 | 48 |

4. Curl Retention

The DMM-containing compositions provided similarly effective curl retention properties as compared to the same compositions without DMM.

5. Hair Characteristics on Tresses

The presence of DMM in the composition did not affect the performance characteristics of the polymers as assessed subjectively on hair tresses (stiffness, tackiness, combability and feel).

6. Films on Glass

All the systems tested gave clear films on glass.

In summary, these results show that dimethoxymethane-containing hydroalcoholic pump hair spray formulations provided a substantial improvement in drying times, and a reduction in curl droop, without affecting curl retention, or other performance characteristics in hair use.

While the invention has been described with particular reference to certain embodiments thereof, it will be understood that changes and modifications may be made which are within the skill of the art. Accordingly, it is intended to be bound only by the following claims, in which:

What is claimed is:

1. A non-aerosol pump, low VOC hydroalcoholic hair spray composition consisting essentially of a hair fixative polymer at a solids level of about 1-15%, an alcohol content of about 50-70%, a water content of about 10-30%, and dimethoxymethane in an amount of about 10-30%, by weight of the composition.

2. A composition according to claim 1 wherein said alcohol is ethanol.

3. A composition according to claim 1 wherein said polymer is a maleic anhydride-alkyl vinyl ether copolymer, a polyvinylpyrrolidone-vinyl acetate copolymer, a vinylpyrrolidone-vinyl caprolactam-dimethylaminoethyl methacrylate terpolymer, or a vinyl acetate-mono-n-butyl maleate-isobornyl acrylate terpolymer.

4. A composition according to claim 1 consisting essentially of a hair fixative polymer at a solids level of about 3-10%, the alcohol is ethanol present in an amount of about 55-65%, water is present in an amount of about 15-25%, and dimethoxymethane is present in an amount of about 15-25%.

* * * * *